United States Patent [19]
Srisathapat et al.

[11] Patent Number: 5,514,103
[45] Date of Patent: May 7, 1996

[54] MEDICATION INFUSION PUMP WITH IMPROVED PRESSURE RESERVOIR

[75] Inventors: Chad Srisathapat, Sun Valley; Virote Indravudh, Saugus, both of Calif.

[73] Assignee: Minimed Inc., Sylmar, Calif.

[21] Appl. No.: 259,440

[22] Filed: Jun. 14, 1994

[51] Int. Cl.$^6$ ............................................. A61M 37/00
[52] U.S. Cl. ............................................. 604/141; 604/131
[58] Field of Search ................................... 604/132, 141, 604/131, 140

[56] References Cited

U.S. PATENT DOCUMENTS

| | | | |
|---|---|---|---|
| 3,951,147 | 4/1976 | Tucker et al. | 604/132 |
| 4,373,527 | 2/1983 | Fischell . | |
| 4,573,994 | 3/1986 | Fischell et al. . | |
| 4,978,338 | 12/1990 | Melsky et al. | 604/132 |
| 5,167,633 | 12/1992 | Mann et al. . | |
| 5,176,641 | 1/1993 | Idriss . | |

Primary Examiner—John G. Weiss
Attorney, Agent, or Firm—Kelly Bauersfeld & Lowry

[57] ABSTRACT

An implantable medication infusion pump is provided of the type having a pressure reservoir with a selected pressure fluid therein for maintaining liquid medication in an adjacent medication chamber under a substantially constant pressure. The reservoir comprises a hollow structural enclosure defined by at least one movable wall and adapted to be filled with a selected quantity of the pressure fluid, particularly such as a selected fluorocarbon in a liquid-vapor state. The movable wall of the pressure reservoir is shared with and defines one side of the medication chamber, with the pressure fluid undergoing appropriate change of state to expand or contract the pressure reservoir in a manner maintaining the medication under substantially constant pressure. The improved pressure reservoir includes an internal spacer element to prevent contraction of the pressure reservoir beyond a minimum volume at least slightly greater than the liquid state volume of the pressure fluid therein. With this construction, at least some pressure fluid within the pressure reservoir remains in a vapor state at all times.

17 Claims, 2 Drawing Sheets

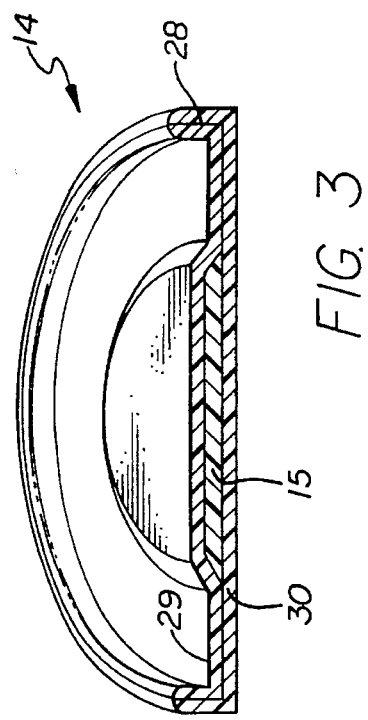
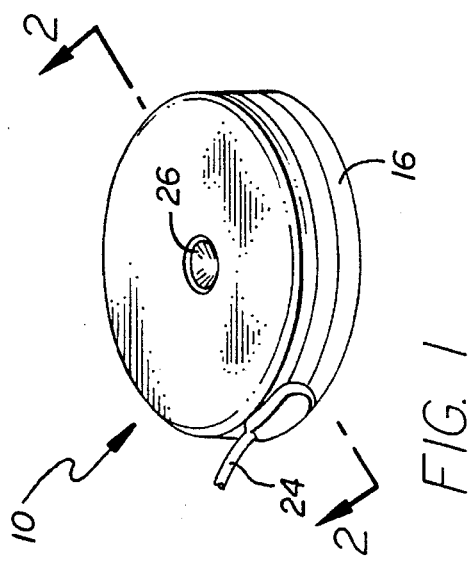
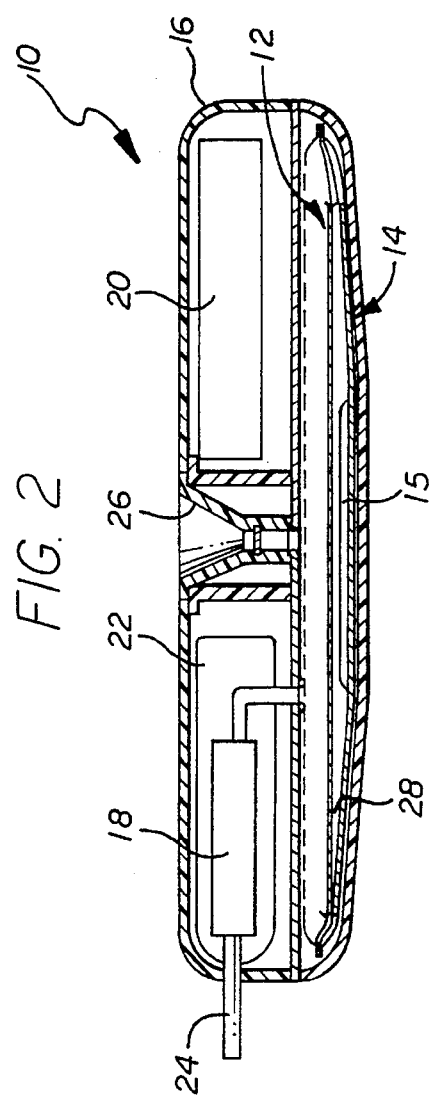

MEDICATION INFUSION PUMP WITH IMPROVED PRESSURE RESERVOIR

BACKGROUND OF THE INVENTION

This invention relates generally to medication infusion pumps particularly of the type designed for implantation directly into the body of a patient and for programmed operation to deliver medication to the patient. More specifically, this invention relates to an improved implantable infusion pump having a simplified fluid pressure reservoir charged with a selected pressure fluid in liquid-gas phase for maintaining a supply of a selected medication under controlled pressure conditions. The improved pressure reservoir incorporates internal spacer means for preventing complete phase change of the selected pressure fluid to a liquid state.

Medication infusion pumps are generally known in the art for use in delivering a selected medication to a patient in a scheduled or preprogrammed manner. In recent years, such infusion pumps have been developed in compact form adapted for direct implantation into the body of a patient, and to deliver a specific medication such as insulin to the patient in discrete doses over an extended period of time. An implanted infusion pump of this general type includes an internal medication chamber for receiving and storing a supply of the selected medication in liquid form, with the medication being subjected to a predetermined storage pressure to insure accurate and repeatable delivery conditions through the use of a miniature pump and associated programmed control means. In many cases, the storage pressure is desirably less than ambient body pressure to prevent undesired leakage of the medication from the medication chamber into the body of the patient, and thereby positively prevent accidental overdose during certain failure modes. For one illustrative example of an implanted medication infusion pump of this general type, see U.S. Pat. No. 4,573,994.

In the past, the medication within the pump medication chamber has been subjected to the desired storage pressure by forming at least a portion of the medication chamber as a movable wall shared with a pressure reservoir charged with a selected pressure fluid. More particularly, the pressure fluid has been provided in a combined liquid-vapor state such as a selected fluorocarbon, wherein the pressure fluid undergoes liquid-vapor change of state at normal body temperature to appropriately expand or contract the pressure reservoir in a a manner acting through the movable wall to maintain the medication chamber under substantially constant pressure conditions. As the medication chamber is expanded upon filling with the medication, the pressure fluid undergoes significant state change to the liquid phase to reduce the volumetric size of the pressure reservoir. Conversely, as the medication is delivered in doses to the patient, the pressure fluid progressively undergoes state change to the vapor phase to reduce the volumetric size of the medication chamber and maintain the medication under substantially constant pressure. Freon 113 has been used to maintain the medication at a slight negative or subambient pressure in response to normal patient body temperature and altitudinal variations up to about 8,500 feet above sea level.

In many prior implantable infusion pumps, the movable wall separating the pressure reservoir from the medication chamber has been constructed in the form of metal foil diaphragm or bellows devices which are relatively costly to manufacture and/or have exhibited unacceptable or unreliable operating performance. More recently, an improved and significantly simplified pressure reservoir has been proposed in the form of a flexible sack or bag constructed from an elastomer material and charged with the selected pressure fluid. See, for example, U.S. Pat. No. 5,167,633.

A flexible elastomer pressure reservoir offers significant advantage in terms of reduced manufacturing cost and complexity, in addition to a reduced volumetric reservoir size which increases the medication-containing capacity of the infusion pump and/or reduces the overall size of the infusion pump. However, when the medication chamber is completely filled with liquid medication, the pressure fluid within the elastomer reservoir may encounter complete phase change to a liquid state within the pressure reservoir. When such complete phase change occurs, renucleation of the liquid pressure fluid to the vapor phase may not occur spontaneously, but instead may require significant additional input energy. In this regard, normal dispensing of the medication to the patient in small doses may not displace the movable wall of the reservoir with sufficient energy to insure pressure fluid renucleation to the vapor state. Accordingly, if the pressure fluid is allowed to change entirely to the liquid state, further phase change back to the vapor state might not occur during normal pump operation whereby the pressure reservoir may fail to maintain the medication under the desired constant pressure conditions.

There exists, therefore, a need for an improved pressure reservoir in an implantable medication infusion pump, particularly with respect to providing means for preventing complete pressure fluid phase change to the liquid state. The present invention fulfills this need and provides further related advantages.

SUMMARY OF THE INVENTION

In accordance with the invention, an implantable medication infusion pump adapted for implantation into the body of a patient is provided with an improved and simplified pressure reservoir for maintaining a selected liquid medication under substantially constant pressure conditions. The pressure reservoir is formed as a hollow structural enclosure adapted to contain a selected liquid-gas phase pressure fluid, with at least a portion of the reservoir enclosure defining a movable wall shared with a medication chamber. The pressure fluid is selected to expand and contract by appropriate liquid-gas phase change as the medication chamber is respectively emptied or filled to subject the medication within the medication chamber to substantially constant pressure conditions. An internal spacer element is mounted within the pressure reservoir to insure that the pressure reservoir volume is at all times at least slightly greater than the volume of the pressure fluid in liquid state. As a result, at least a small portion of the pressure fluid remains at all times in a vapor state, thereby preventing complete state change of the pressure fluid to the liquid form.

In one preferred embodiment of the invention, the pressure reservoir comprises a flexible sack or bag having an appropriate disk or other suitable shape for mounting into the housing of an implantable infusion pump. The reservoir bag is constructed from a flexible elastomer material such as Halar plastic chosen for its compatibility and relative impermeability to a fluorocarbon pressure fluid such as Freon 113. Prior to closure and sealing of the reservoir bag, the spacer element is installed into the bag interior. In one preferred form, the spacer comprises a porous plastic member having a disk or other suitable shape and having an internal open volume which is at least slightly greater than the liquid state volume of pressure fluid to be contained within the reservoir bag. The reservoir bag is then charged with the appropriate quantity of the pressure fluid and sealed, followed by mounting into the pump housing with at least one side of the bag cooperating with the housing to define the medication chamber.

In alternative preferred forms, the reservoir bag may have a semicircular or other suitable shape adapted for compact and space-efficient mounting into a pump housing with one side of the bag defining a portion of the medication chamber. The spacer element may be provided as one or more small blocks or other structural members designed to prevent bag collapse beyond a minimum volumetric size at least slightly greater than the liquid state volume of pressure fluid to be contained within the bag. The preferred spacer members have a porous construction defining an open internal volume or otherwise insuring the presence of voids within the bag, wherein the open internal volume or voids at least slightly exceed the liquid state volume of the pressure fluid.

Other features and advantages of the present invention will become more apparent from the following detailed description, taken in conjunction with the accompanying drawings which illustrate, by way of example, the principles of the invention.

BRIEF DESCRIPTION OF THE DRAWINGS

The accompanying drawings illustrate the invention. In such drawings:

FIG. 1 is a perspective view of an implantable medication infusion pump adapted for implantation into the body of a patient, and further adapted to include the improved liquid-vapor pressure reservoir embodying the novel features of the invention;

FIG. 2 is an enlarged vertical sectional view taken generally on the line 2—2 of FIG. 1, and illustrating the improved pressure reservoir of the present invention;

FIG. 3 is a fragmented perspective view depicting the improved pressure reservoir construction;

DETAILED DESCRIPTION OF THE PREFERRED EMBODIMENTS

Figure 4:
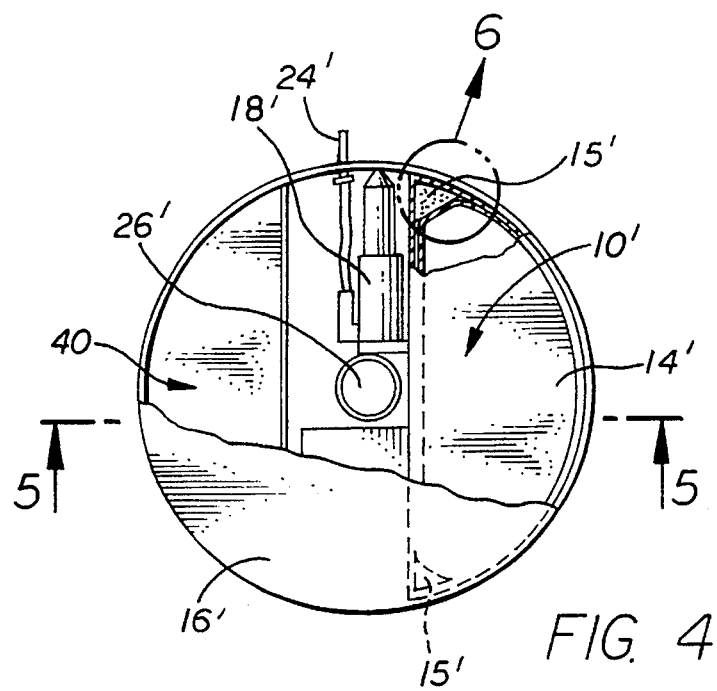
FIG. 4 is a top plan view depicting an alternative configuration for an implantable infusion pump having a liquid-vapor pressure reservoir of an alternative preferred geometry mounted therein.

As shown in the exemplary drawings, an implantable medication infusion pump referred to generally in FIGS. 1 and 2 by the reference numeral 10 is provided for use in administering a selected medication to a patient in a controlled, preprogrammed manner. The infusion pump 10 receives and stores a quantity of a selected medication within an internal medication chamber 12 (FIG. 2), wherein the medication is subjected to a predetermined and substantially constant pressure through the use of an improved and simplified pressure reservoir 14 charged with a selected pressure fluid in a combined liquid-gas state. A spacer element 15 is mounted within the pressure reservoir 14 and functions to prevent complete state change of the pressure fluid to the liquid phase.

The illustrative medication infusion pump 10 comprises a small and substantially self-contained unit for direct implantation in the body of a patient. The pump 10 comprises an hermetically sealed pump housing 16 formed from a biocompatible material such as titanium or titanium alloy. The pump housing 16 defines the internal medication chamber 12 for receiving and storing the supply of the selected medication in liquid form, such as insulin for a diabetic patient. The pump housing 16 further encases a miniature dispensing pump 18 and associated electronic control circuitry 20 in combination with a battery 22 for periodically operating the pump 18 to deliver medication doses from the chamber 12 to the patient via an appropriate catheter 24 or the like. The control circuitry is suitably preprogrammed to deliver the medication in accordance with individual patient need. An inlet or refill fitting 26 on the pump housing 16 is adapted to receive a hypodermic needle (not shown) to permit percutaneous refilling of the medication chamber 12 without requiring surgical access to the infusion pump 10. For a more detailed description of the overall construction and operation of the implantable infusion pumps of this general type, see U.S. Pat. Nos. 4,373,527 and 4,573,994 which are incorporated by reference herein.

As is known in the art, the infusion pump 10 includes the variable volume pressure reservoir 14 mounted within the pump housing 16 with at least one wall of the pressure reservoir 14 exposed to and thereby defining at least a portion of the medication chamber 12. More particularly, the liquid-gas phase pressure fluid within the pressure reservoir 14 is adapted to vary the volumetric size of the medication chamber 12 in accordance with the quantity of medication therein to maintain the medication under substantially constant pressure conditions. A preferred pressure fluid comprises a fluorocarbon which has a substantially linear pressure characteristic as it changes from liquid to vapor state and vice versa at normal human body temperature and at a normal range of altitudes. A preferred pressure fluid is Freon 113 which assumes a liquid-vapor state at normal body temperature and at altitudinal variations up to about 8,500 feet above sea level to exert a slightly negative and substantially constant pressure of about −2.5 to −4.0 psi on the medication chamber 12. This slight negative pressure beneficially confines the medication against undesired leakage from the pump housing 16 into the body of the patient. Alternately, other liquid-vapor pressure fluids are known in the art for applying other specific pressures to the medication, such as a slight positive pressure as may be required for some implantable pump designs.

The pressure reservoir 14 shown in FIGS. 2 and 3 comprises a flexible and expansible sack or bag 28 shown with a generally disk shape and defined by circular sheets 29 and 30 of plastic film material connected about their peripheries by heat sealing or the like to form a hollow structural enclosure. This flexible bag 28 is formed as a structural unit separate from the remaining components of the infusion pump 10, with a preferred elastomeric material for the sheets 29 and 30 being sold under the name Halar by Allied Corporation of Morristown, New Jersey. In this regard, Halar film is especially suited for use in the environment of implantable infusion pumps due to its relatively high compatibility with and impermeability to fluorocarbon pressure fluids, such as Freon 113. For a more detailed discussion regarding the general construction of the reservoir bag 28 and alternative geometries therefor, see U.S. Pat. No. 5,167,633, entitled MEDICATION INFUSION PUMP WITH IMPROVED LIQUID-VAPOR PRESSURE RESERVOIR, which is incorporated by reference herein.

In operation, the liquid-vapor pressure fluid within the flexible reservoir bag 28 expand s and contracts the bag volume in a manner varying inversely with the volume of medication within the medication chamber 12. In particular, as the medication chamber 12 is filled with medication, the pressure fluid undergoes appropriate change of state to the liquid phase in a progressive manner and to the extent necessary to maintain the medication under a substantially constant pressure. As the medication is dispensed to the patient through the catheter 24, the pressure fluid undergoes progressive or gradual state change to the vapor phase with corresponding expansion of the reservoir bag 28 sufficiently to maintain the remaining medication in the chamber 12 under substantially constant pressure. The spacer element 15 is provided to prevent the reservoir bag from collapsing or contracting beyond a minimum volume configuration which would permit complete state change of the pressure fluid to the liquid phase. Prevention of such complete state change to the liquid phase is desirable, since significant energy may be required to reinitiate or renucleate state change to the vapor phase, wherein normal medication doses administered to the patient would provide inadequate energy to reinitiate vapor phase nucleation. Instead, the spacer element 15 insures that at least a small portion of the pressure fluid remains in the vapor phase at all times, such that the minimal energy levels associated with medication dispensing will provide broad range state change to maintain substantially constant pressure conditions as the medication chamber is refilled and emptied.

As shown in FIGS. 2 and 3, the preferred spacer element 15 comprises a generally disk-shaped member installed into the interior of the reservoir bag 28 to occupy a portion of the internal volume thereof. The preferred spacer member comprises a porous plastic material having an open internal volume for absorbing the pressure fluid, and which at least slightly exceeds the liquid phase volume of the pressure fluid within the reservoir bag. With this construction, complete filling of the medication chamber 12 results in substantial volumetric collapse of the reservoir bag 28 and a corresponding substantial phase change of the pressure fluid to the liquid state. However, the residual open internal volume provided by the spacer element 15 prevents complete pressure fluid state change to the liquid phase. As a result, complete filling of the medication chamber 12 with liquid medication is ineffective to collapse the reservoir bag 28 to a volumetric size equalling the liquid volume of the pressure fluid. At least a small portion of the pressure fluid therefore remains in the vapor phase at all times, such that renucleation energy to reinitiate vapor state phase change is not required.

The specific design and geometry of the spacer element 15 may vary widely so long as the minimum internal volume is maintained. A preferred spacer element 15 comprises a porous polyethylene disk or filter which is generally compatible with the pressure fluid and has a porosity and sufficient thickness to absorb a liquid volume at least slightly exceeding the liquid state volume of the pressure fluid within the reservoir 14. Alternately, an annular ring or other suitable structure such as a notched or slotted disk or the like may be provided to define the desired minimum internal bag volume when the medication chamber 12 is filled. In any case, a smooth external surface for the spacer element 15 is desired to prevent abrasive contact with the bag materials as the reservoir expands and contracts.

Figure 5:
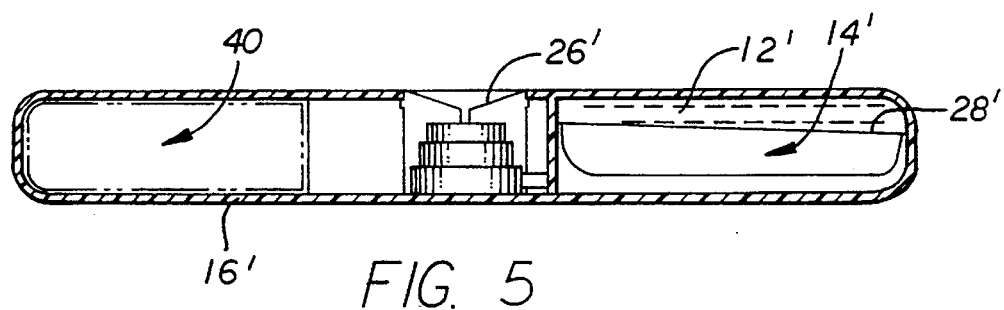
FIG. 5 is an enlarged vertical sectional view taken generally on the line 5—5 of FIG. 4.
Figure 6:
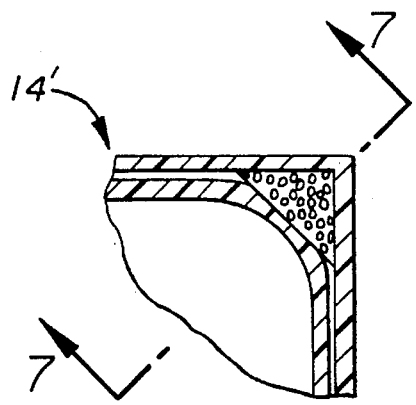
FIG. 6 is an enlarged fragmented sectional view corresponding generally with the encircled region 6 of FIG. 4.
Figure 7:
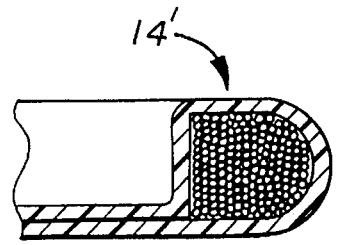
FIG. 7 is an enlarged fragmented vertical sectional view taken generally on the line 7—7 of FIG. 6.

An alternative geometry for a medication infusion pump 10' is shown in FIGS. 4–7, wherein components corresponding in function with those shown and described in FIGS. 1–3 are identified by common primed reference numerals. As shown, the pump 10' includes a pump housing 16' with a pressure reservoir 14' of generally semicircular shape contained therein in combination with a small pump 18' operated by an associated battery and control circuitry referenced generally by numeral 40 in FIGS. 4 and 5 to dispense medication from a medication chamber 12' to a patent via a catheter 24". As inlet fitting 26' permits percutaneous refilling of the reservoir 14'.

The semicircular reservoir 14' is again formed as a flexible bag 28' from interconnected sheets of Halar plastic film or the like and is adapted to be charged with the selected liquid-gas pressure fluid with one side exposed to the medication chamber 12'. One or more spacer elements 15' (FIGS. 4, 6 and 7) are installed at selected positions within the bag interior, such as at opposite corners of the semicircular bag, with a preferred spacer element construction comprising a porous plastic material. The combined open internal volume provided by the spacer elements 15' by themselves or in combination with residual volume within the bag 28' insures that at least a portion of the pressure fluid remains in a vapor state at all times.

A variety of further modifications and improvements to the improved implantable infusion pump of the present invention will be apparent to those skilled in the art. For example, while the spacer element or elements have not been described as fixed within the associated reservoir bag at any specific locations, it will be understood that a suitable adhesive or the like may be used to fix the spacer elements in place, if desired. Accordingly, no limitation on the invention is intended by the foregoing description and accompanying drawings, except as set forth in the appended claims.

What is claimed is:

1. A medication infusion pump, comprising:

a pump housing having a medication chamber formed therein for receiving a supply of a selected medication;

pump means within said housing for delivering the medication from said medication chamber to a patient;

a pressure reservoir having a selected liquid-vapor pressure fluid therein, said pressure reservoir being mounted within said pump housing and defining a movable wall exposed to said medication chamber, said pressure fluid being adapted to undergo sufficient liquid-vapor phase change for expanding and contracting the volumetric size of said pressure reservoir in response to the quantity of the medication within said medication chamber to maintain the medication under a predetermined and substantially constant pressure: and spacer means within said reservoir for preventing contraction of the pressure reservoir beyond a minimum open internal volume at least slightly greater than the liquid phase volume of the pressure fluid, whereby at least a portion of the pressure fluid remaining in a vapor phase at all times.

2. The medication infusion pump of claim 1 wherein said pressure reservoir is formed as an expansible bag.

3. The medication infusion pump of claim 1 wherein said spacer means comprises at least one porous spacer member having an open internal volume at least slightly greater than the liquid phase volume of the pressure fluid.

4. The medication infusion pump of claim 1 wherein said spacer means comprises at least one porous spacer member for absorbing the pressure fluid.

5. The medication infusion pump of claim 4 wherein at least one said spacer member cooperates with said reservoir to define said open internal volume.

6. The medication infusion pump of claim 4 wherein said spacer member comprises a disk of porous plastic material.

7. The medication infusion pump of claim 1 wherein said pressure reservoir has a generally disk shape.

8. The medication infusion pump of claim 1 wherein said pressure reservoir has a generally semicircular shape.

9. The medication infusion pump of claim 1 wherein said pressure fluid is a selected fluorocarbon.

10. The medication infusion pump of claim 1 wherein said spacer means has a smooth exterior surface.

11. A pressure reservoir for use with a medication pump for maintaining a selected medication within a medication chamber under a predetermined and substantially constant pressure, said reservoir comprising;

means defining an expansible structural enclosure with a movable wall exposed to said medication chamber;

a selected liquid-vapor pressure fluid within said enclosure, said pressure fluid being adapted to undergo sufficient liquid-vapor phase change for expanding and contracting the volumetric size of said enclosure in response to the quantity of the medication within said medication chamber to maintain the medication chamber under a predetermined and substantially constant pressure; and spacer means within said enclosure for preventing contraction of said enclosure beyond a minimum open internal volume at least slightly greater than the liquid phase volume of the pressure fluid, whereby at least a portion of the pressure fluid remaining in a vapor phase at all times.

12. The pressure reservoir of claim 11 wherein said enclosure is formed as an expansible bag.

13. The pressure reservoir of claim 11 wherein said spacer means comprises at least one porous spacer member having an open internal volume at least slightly greater than the liquid phase volume of the pressure fluid.

14. The pressure reservoir of claim 11 wherein said spacer means comprises at least one porous spacer member for absorbing the pressure fluid.

15. The pressure reservoir of claim 14 wherein at least one said spacer member cooperates with said enclosure to define said open internal volume.

16. The pressure reservoir claim 14 wherein said spacer member comprises a disk of porous plastic material.

17. The pressure reservoir of claim 11 wherein said pressure fluid is a selected fluorocarbon.

* * * * *